(12) United States Patent
Gonon

(10) Patent No.: US 6,423,028 B1
(45) Date of Patent: Jul. 23, 2002

(54) PROCESS FOR GENERATING A PULSATILE STREAM OF A PULSED-SUCTIONED STERILE FLUID JET AND RESULTING PULSED JET FOR A HANDPIECE, IN PARTICULAR FOR SURGICAL USE

(75) Inventor: Bertrand Gonon, Lyons (FR)

(73) Assignee: Saphir Medical, Dardilly (FR)

( * ) Notice: Subject to any disclaimer, the term of this patent is extended or adjusted under 35 U.S.C. 154(b) by 0 days.

(21) Appl. No.: 09/335,880

(22) Filed: Jun. 18, 1999

(30) Foreign Application Priority Data

Jun. 19, 1998 (FR) .......................... 98 07879
Mar. 22, 1999 (FR) .......................... 99 03630

(51) Int. Cl.$^7$ ............................................. A61M 1/00
(52) U.S. Cl. .......................................... 604/35; 604/28
(58) Field of Search ............................ 604/35, 30, 31, 604/32, 36, 118–121

(56) References Cited

U.S. PATENT DOCUMENTS

| | | | |
|---|---|---|---|
| 4,205,677 A | 6/1980 | Engstrom | 128/276 |
| 4,519,385 A | 5/1985 | Atkinson et al. | 128/66 |
| 4,655,197 A | 4/1987 | Atkinson | |
| 4,676,779 A | 6/1987 | Mayoral | 604/65 |
| 4,702,733 A | 10/1987 | Wright et al. | 604/34 |
| 4,759,349 A | 7/1988 | Betz et al. | 128/6 |
| 5,322,506 A | 6/1994 | Kullas | 604/30 |
| 5,605,537 A | 2/1997 | Ivey | 604/21 |
| 5,674,226 A | 10/1997 | Doherty et al. | |
| 5,735,815 A | 4/1998 | Bair | 604/51 |
| 5,788,667 A * | 8/1998 | Stoller | 604/22 |

FOREIGN PATENT DOCUMENTS

| | | |
|---|---|---|
| DE | 30 19 115 A1 | 12/1981 |
| DE | 37 15 418 A | 11/1987 |
| EP | 0 346 712 A2 | 12/1989 |
| EP | 0 470 781 A1 | 2/1992 |
| EP | 0 489 496 A1 | 6/1992 |
| EP | 0 489 496 A | 6/1992 |
| EP | 0 551 920 A1 | 7/1993 |
| EP | 0 636 345 A1 | 2/1995 |
| EP | 0 879 578 A1 | 11/1998 |
| EP | 0 888 750 A1 | 1/1999 |
| FR | 1 378 042 | 2/1965 |
| FR | 2 706 276 | 12/1994 |
| WO | WO 94/10917 | 5/1994 |
| WO | WO 94 28807 | 12/1994 |
| WO | WO 96/01079 | 1/1996 |
| WO | WO 96/35469 | 11/1996 |
| WO | WO 96/39952 | 12/1996 |
| WO | 97/03713 | 2/1997 |
| WO | WO 97/49441 | 12/1997 |
| WO | WO 98/55033 | 12/1998 |
| WO | WO 99/33510 | 7/1999 |

\* cited by examiner

*Primary Examiner*—Manuel Mendez
*Assistant Examiner*—Ann Y. Lam
(74) *Attorney, Agent, or Firm*—Armstrong, Westerman, Hattori, McLeland & Naughton, LLP

(57) ABSTRACT

The process consists in generating a firing pulse pattern characterized in that it implements a pressurized liquid channel and a pneumatic aspiration channel and in that the periodic firing of the pressurized jet is controlled during the periodic application of aspiration and in that the tension on the tissue is released during the cutoff of the aspiration by aeration.

A variant of the process enables obtaining, even in the case of a high repetition rate, a steep trailing edge of the firing pulse, by means of establishment of communication with the exterior of the pressurized liquid feed line near the time of the cutoff of the feeding of the liquid.

This invention is of interest to manufacturers of surgical and medical instruments and handpieces for interventions using a pressurized liquid jet.

25 Claims, 6 Drawing Sheets

PROCESS FOR GENERATING A PULSATILE STREAM OF A PULSED-SUCTIONED STERILE FLUID JET AND RESULTING PULSED JET FOR A HANDPIECE, IN PARTICULAR FOR SURGICAL USE

The invention concerns a process for generation of a pulse train of a pulsed-aspirated sterile liquid jet and the pulsed-aspirated liquid jet thus generated to feed a handpiece or a catheter, in particular for surgical and medical applications.

The use of pulsed jets of a sterile liquid under high pressure for surgical purposes is already known.

It is possible, for example, to cite in this regard EP 0636345 in the name of SENTINEL MEDICAL, which concerns a surgical instrument with a pulsed liquid jet for cutting and emulsification along with aspiration for evacuation of the liquid and biological residues.

The pulsed jet is produced by the repeated back and forth motion of an amplifier piston which receives the liquid under depression.

The major disadvantage of this system concerns the use of a piston which can produce only a single pulse train during its working stroke along its path. It is then necessary to refill the piston chamber, a fact which limits this device to discontinuous operation, which is not very compatible with the requirements of the work of surgeons.

There are also inventions associated with eye surgery in which a pulsed liquid jet is directed at the eye, at the cornea in particular, to disintegrate defective tissues and to dislodge deposited or encrusted materials and bodies. These inventions are protected by U.S. Pat. Nos. 3,818,913 and 3,930,505 in the name of WALLACH.

These are high frequency pulsed jets intended for the high repetition rate of disintegration work by a train of impacts for cleaning the crystalline lens by clearing it of defective tissues and foreign bodies and materials. Separate aspiration is provided conventionally for the evacuation of the liquid and residues from the disintegration procedure.

In these last devices, the aspiration is also continuous and separate. In contrast, this is not cutting but rather dislodging and disintegration for the purpose of evacuation of the unwanted tissues and materials.

In general, the high-pressure pulsed liquid jets of the prior art are liquid pulse trains triggered on demand and sprayed onto the dissection zone.

The liquid sprayed is then evacuated by aspiration continuously or when it exceeds a certain quantity deemed to interfere with the continuation of the dissection work.

In these implementations, the surgeon cannot approach the tissue to be dissected too closely with the end of the handpiece because of lateral spraying of liquid and the splattering thus generated interfering with the visibility of the operative field.

Moreover, the dissection yield is only slightly better than that with a continuous jet because of the rebound phenomena.

And finally, the penetration of liquid, even though it is sterile, into the incision in small but non-negligible quantities is a disadvantage for the body of the patient, which must eliminate it in addition to all the other stresses associated with the surgery.

The object of the present invention is to remedy the aforementioned disadvantages by proposing a process for generation of a pulsed train of a pulsed-aspirated sterile liquid jet and the pulsed-aspirated jet thus generated to feed a handpiece, a catheter, or the like, intended for surgical or medical applications.

According to the basic process, the firing of elementary pressurized liquid jets is periodically controlled by opening and cutting the flow of the pressurized liquid feeding the handpiece periodically at a repetition rate $F_R$. The on and off aspiration is controlled at the same repetition rate at times such that the firing occurs during aspiration, with the cutoff of the aspiration occurring before the next periodic control of the firing of the pressurized liquid jet. This process enables creation of a jet ejected and aspirated with high surgical effectiveness.

To this end, the basic process according to the invention is characterized in that a pressurized liquid channel, under high pressure, for example, and a pneumatic aspiration channel are used and in that the firing of the pressurized jet is controlled periodically during the periodic application of the aspiration and in that the tissue is released during the interruption of the aspiration by aeration.

The process according to the invention presents numerous advantages.

It enables avoiding lateral spraying and splashing of any type and because of this, it offers good visibility of the operative field at the same time as the possibility of very closely approaching the tissue to be incised.

Since it is a pulsed-aspirated jet, i.e., a jet fired at the same time as the aspiration is operating, the tissue remains taut, i.e., tight momentarily before and during the firing at the end of the sheath on the end of the handpiece, then relaxes during the final phase of aspiration. Thus, one fires at tight tissue, which ensures precision and cleanness of the incision and of the operative field.

Since the period of application of the jet is short, low consumption of sterile liquid is guaranteed.

During specific phases of the surgical intervention, or for specific applications, it is advantageous to increase the repetition rate of the pressure jet.

However, when the repetition rate of the jet increases, and/or when, after a certain length, the inertia, the elasticity, and the reservoir effect associated with the distortion of the feed tube of the handpiece and the residual pressure become perceptible, this basic procedure becomes less efficient.

In effect, despite the presence of a reinforcing sheath, the high-pressure liquid feed tube becomes slightly distorted. The decaying edge of the pressure pulse does not merely slope but becomes rounded, permitting the appearance of an inefficient zone increasing with the pulse rate which encroaches on the recovery and aspiration zone, such that, beginning with an upper limit of frequencies, one approaches a continuous pattern, losing the advantages associated with the pulsed pattern.

However, the existence of a high-pressure cutting edge which is clean, steep, and of short duration is an important condition for precision, convenience, and efficiency in surgical work.

The object of the variant of the basic process is to remedy these disadvantages.

The inventive principle of this variant consists in obtaining a decaying edge of the pressure pulses of the liquid jet no longer only by cutting the pressure and thus cutting the jet, but rather by establishment of simultaneous or quasi-simultaneous communication of the liquid feed line with the exterior, in particular with the air or with the aspiration or with the vacuum generator.

According to the variant of the basic process, as an offshoot on the pressurized liquid feed tube, a branch line connected to the depression generator or to the air via an opening and closing element controlled at the repetition rate in sync with the other controls is provided in order to discharge the residual pressure existing in the pressurized liquid feed line before the next firing. This periodic control of establishment of communication of the pressure line with the exterior occurs simultaneously or immediately before or after the cutoff command of the high-pressure feed line.

This variant of the process presents various additional advantages:

trailing edge of the pressure pulse marking the very steep termination when the repetition rate increases;

efficiency and cleanness in the surgical work;

an improvement very easy to implement.

Other characteristics and advantages of the invention will appear in the description which follows, provided by way of a nonrestrictive example with reference to the drawings, wherein.

The basic process according to the invention consists in generating, using all appropriate means: mechanical, electric, electromechanical, electromagnetic, or others, under control from a first line transporting a pressurized sterile liquid delivered by a generator and a second pneumatic aspiration line, a pulse train of a pulsed-aspirated sterile liquid jet, and in emitting it by means of the handpiece for medical or surgical applications.

More specifically, for each of the lines, liquid on the one hand and aspiration on the other, a means of sequential closing-opening of flow at the same repetition rate, but with an opening duration which may be different for the two liquids is used.

According to the basic process of the invention, the firing of the pressurized liquid jet, i.e., the opening of the means of closing-opening the liquid line, is effected during the aspiration time intervals, i.e., during the open period of the means of closing-opening the aspiration line.

The process is completed in that neutralization of the aspiration is performed by vacuum immediately after the closing of the aspiration line, for example, by aerating the aspiration line to block the aspiration.

The basic process can be implemented by simple means, such as electromechanical means with push rods or other means acting by pinching or crushing a flexible line carrying the liquid or the aspirated air or by hydraulic cutoff components such as flow throttling devices or solenoid valves, all controlled by an electronic sequencing circuit.

The same is true for the means of periodic aeration of the aspiration line enabling dislodging of the tissue to be incised from the aspirating end of the handpiece, for which the means of closing-opening are pneumatic and no longer hydraulic.

Preferably, aeration is carried out via the aspiration line, for example, via an offshoot thereof periodically opened and closed, but any other means of compensating the suction force to relax the tissue is possible.

The process will now be explained with reference to the various waveforms.

Figure 1:
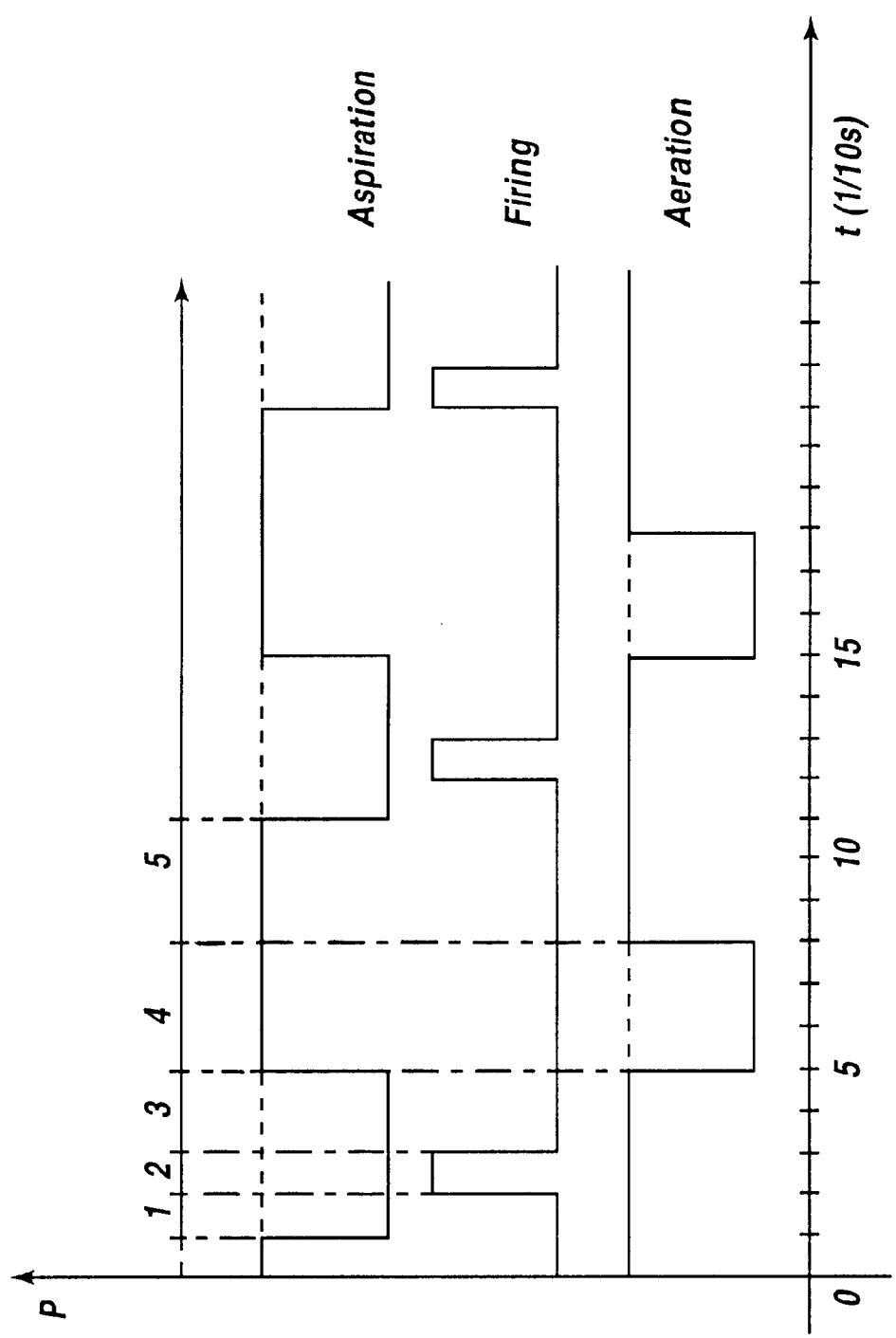
FIG. 1 is a graphic of the basic waveforms of the parameters of the pulse train as a function of time.

The main phases characteristic of each period of the pulse train according to the invention, referenced by the numbers 1 through 5 in FIG. 1, are the following:

phase 1: start of aspiration, phase 2: firing of the pressurized jet for a short period within the aspiration pulse, phase 3: continuation of aspiration after firing, phase 4: aeration during cutoff of aspiration, phase 5: continuation of cutoff of aspiration until the next period.

The following general characteristics are seen in the figures. Firing occurs with a certain delay relative to the beginning of aspiration. Firing occurs preferably within the first half of the aspiration pulse width and stops preferably before the end of the second half. Aeration occurs after the aspiration is cut off and preferably, but not imperatively, immediately after this cutoff.

The main characteristic values of the parameters of the pressurized pulsed-aspirated liquid jet pulse train corresponding to that depicted in FIG. 1 are indicated as a nonrestrictive example.

repetition rate ($F_R$): 1 Hz width of firing pulse: 100 ms width of aspiration pulse: 400 ms aspiration pause: 600 ms width of aeration pulse: 300 ms lag between the end of the aspiration pulse and aeration: short.

Aeration is short in duration and quickly follows the end of aspiration.

The rising edges of the pulses are depicted as vertical. In practice, the slope will depend on the type of closing-opening flow device used, particularly on its inertia.

Other, different waveforms are possible.

Thus, the repetition rate of the pulse pattern and the width of the pulses may be modified. It is thus possible to make modifications as a function of the surgical application, i.e., the type of intervention, organ, or tissue targeted as well as the depth of intervention in the human body.

The device generating this controlled pulse train will enable varying these major parameters, including the time parameters. The repetition rate $F_R$ may, for example, be within a range from a fraction of a hertz to several hertz, for example between 0.1 and 10 Hz.

It should be noted that the more the width of the firing pulse increases, the more that of the aspiration should increase in order to be able to completely evacuate the liquid and the residue(s).

Figure 2:
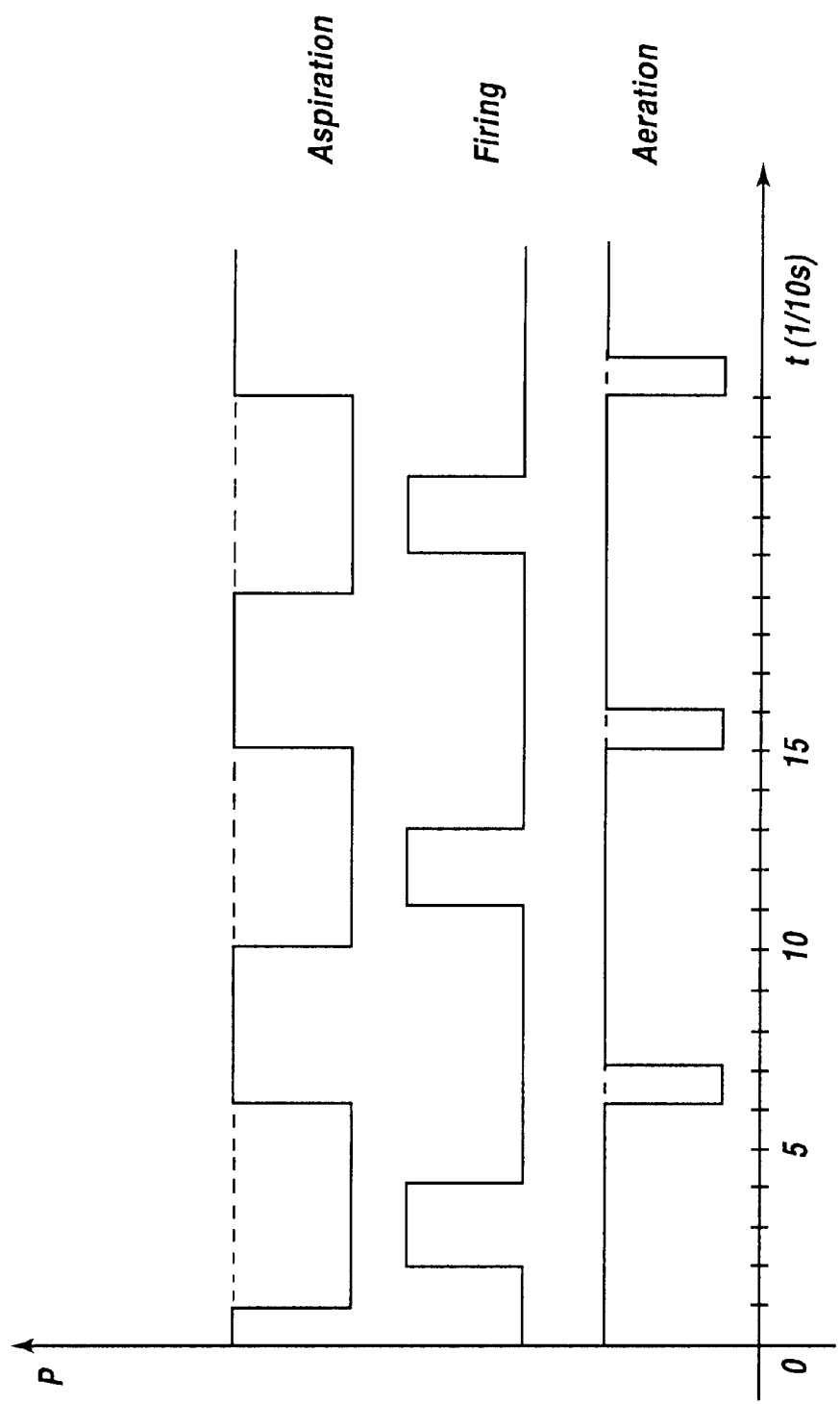
FIG. 2 is a graphic of the waveforms according to a first variant with a longer firing duration.

FIG. 2 depicts waveforms based on the same principle of a pressurized pulsed-aspirated liquid jet, which is the object of the basic process according to the invention. It is noted that the firing period and the aspiration period increase simultaneously. In effect, the longer the firing period, the longer the aspiration should be to be able to evacuate all the liquid sprayed and the solid residues. Co-relatively, the controlled pulses or the openings corresponding to the aeration move on the time axis to begin immediately after the cutoff of aspiration.

Figure 3:
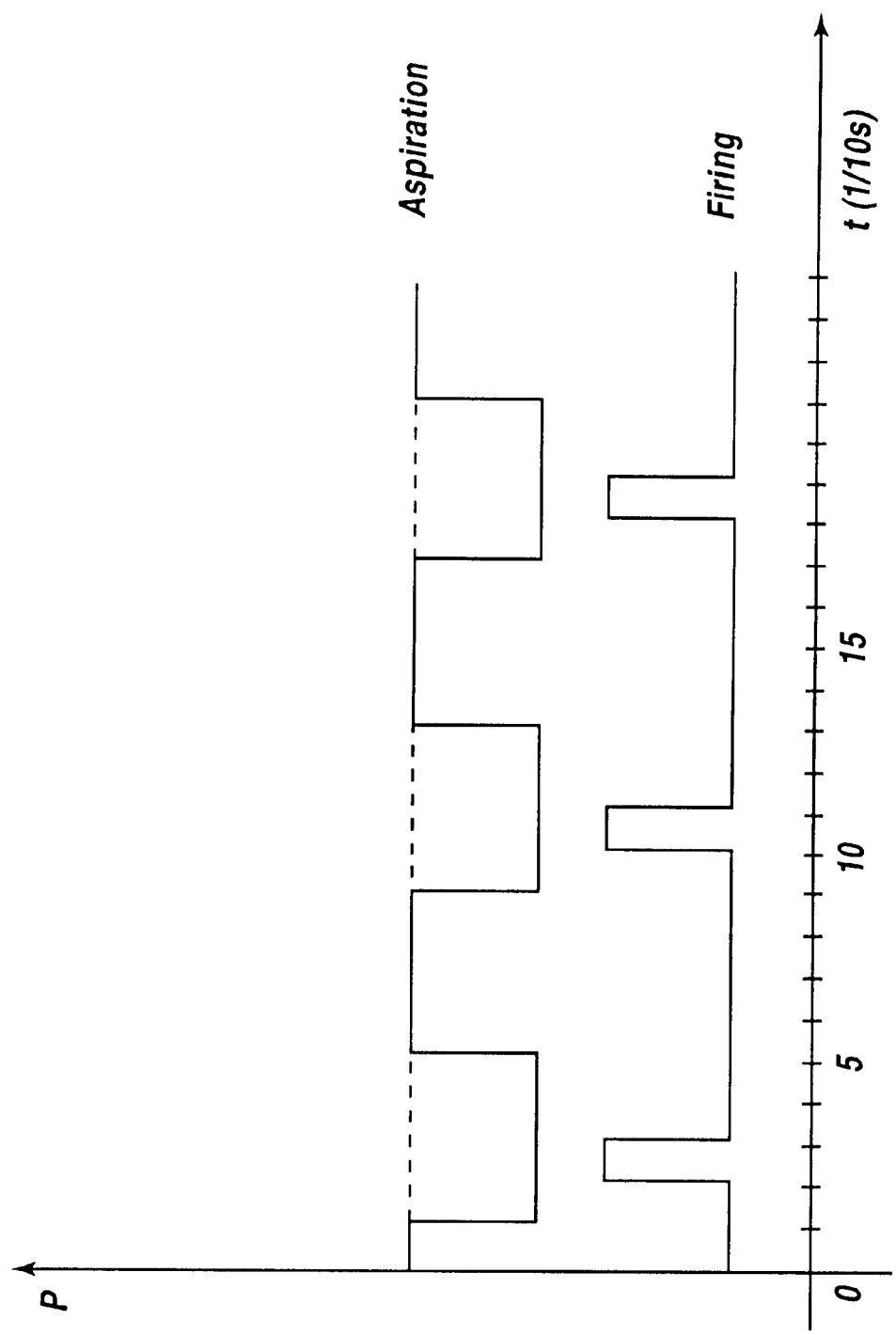
FIG. 3 is a graphic of the waveforms of firings not utilizing aeration.

FIG. 3 depicts waveforms without aeration. This example of application is that of a handpiece with an end sheath open on its periphery, by means of which the relaxation of the tissue after firing is effected automatically after cutoff of the aspiration.

The variant of the basic process according to the invention will now be described.

Figure 4:
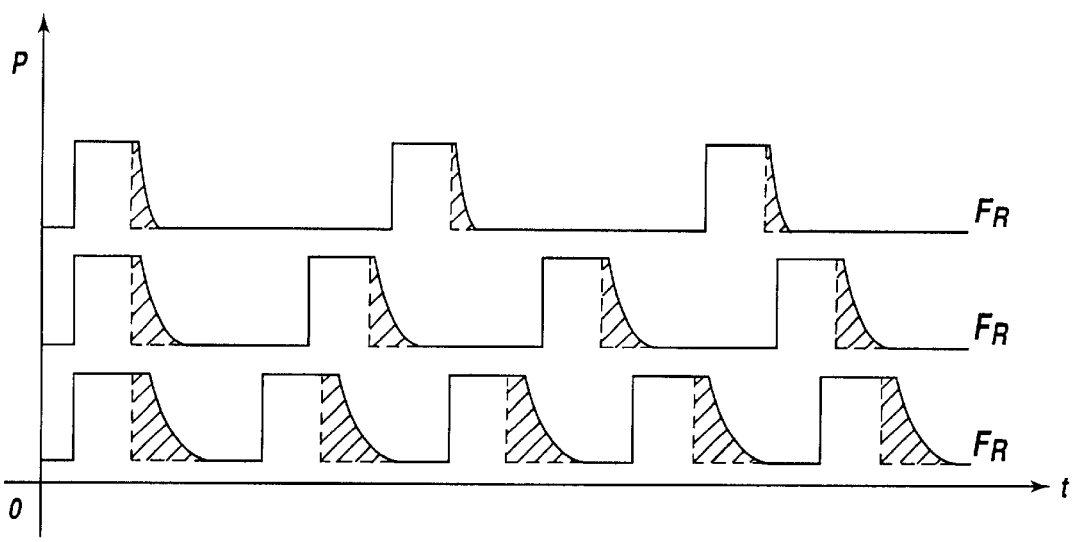
FIG. 4 is a comparative graphic depiction of three pulse trains of pressure P of liquid as a function of the time "t" at increasing repetition rates $F_R$ showing the inefficiency zone of the basic process increasing with the increase in the repetition rate.

FIG. 4 illustrates the problem solved by the variant of the basic process.

When the repetition rate $F_R$ of the periodic pulses of pressure P forming the time base of the pulsed jet increases, a distortion of the decay edge of the pulses occurs.

This distortion worsens with the increase in the rate $F_R$. Moreover, as is discernible from the increase in the area of the hatched zones, the slope and the decay gradient worsen, with the gradient becoming curvilinear or assuming an exponential course.

Along with the ideal vertical trailing edge, this gradient delimits a hatched zone of inefficiency whose size increases with the repetition rate $F_R$. The pulse increases in width by prolongation of its trailing edge, and the pressure cutoff is no longer sharp but becomes gradual.

FIG. 4 permits visualization of this disadvantage.

The slope and distortion of the trailing gradient causes a switching off of the pressure later and later in the time "t", which tends to join the next rising edge of pressure. The pulses could thus become combined and the pattern could tend toward a continuous pattern.

The distortion of the trailing edge and the increase in the width of the liquid pressure pulse reduce the efficiency of the pulsed jet. The repetitive impact effect lessens and thus the significant component of the working efficiency linked to the periodic shocks gradually disappears.

The object of the present improvement is to remedy this disadvantage by correcting the distortion of the trailing edge of the pressure pulse by means of controlled or automatic decompression of the pressurized liquid feed tube of the handpiece. This decompression is synchronized with the pressure pulses.

This variant of the basic process proceeds from the general inventive idea which consists in generation of a pulsed liquid jet pulse train with aspiration in which the feed line of the pressure generator for the liquid is periodically placed in communication with a depression generator or with the air to give rise to a pulse pattern of liquid ejection by a handpiece at a repetition rate $F_R$, in which the trailing edge of the pressure pulse of the liquid is obtained by cutting the feed of pressurized liquid and by discharging the pressure residual which remains or would remain in the pressurized liquid feed line of the handpiece due to communication of this line with the exterior.

According to the basic process, a generator GHP of pressurized liquid, in particular of sterile liquid, is connected to a handpiece 1, or PAM, which is, for example, surgical, by a tubular pressurized feed line 2 via a closing-opening element 3 periodically controlled at a repetition rate $F_R$. The pressurized liquid is, for example, generated and ejected at a pressure between 15 and 100 bar depending on the intended application.

An aspiration circuit includes a depression generator GDP connected to the handpiece 1 by an independent aspiration line 4 through an isolation-communication element 5 controlled at the repetition rate $F_R$ in sync with the closing-opening control of the tubular pressurized liquid feed line 2 by the closing-opening element 3.

An aeration device (not shown) is grafted onto the aspiration line. It is controlled in sync with the other controls at the repetition rate $F_R$. This aeration device serves to neutralize the aspiration and thus to relax the tissue immediately before a new firing.

According to the present variant, an adjacent outlet is provided on the tubular pressurized feed line 2 in the form of a branched offshoot 6 enabling establishment of communication with the exterior.

The general function of this branched offshoot 6 is to periodically establish communication between the pressurized liquid feed line 2 and the exterior. More specifically, this function is that of decompressing, i.e., rapidly evacuating the pressure residual, immediately before or after or at the time of the closing of the pressurized liquid feed line 2.

Figure 5:
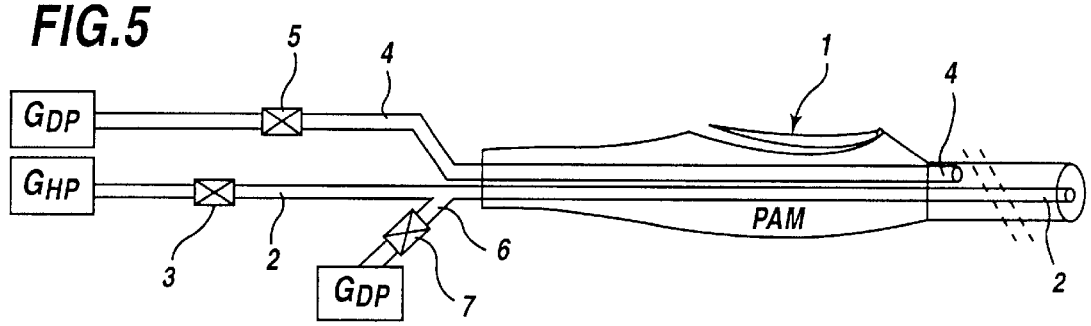
FIG. 5 is a basic assembly view depicting the links with the various sources and the placement of the cutoff-opening elements using a depression generator GDP.

As depicted in FIG. 5, one of the possible means of decompression is connection to a depression generator GDP, which may be the same as that of the aspiration circuit, and with this connection via a switching device 7 providing for controlled opening and closing of the communication with this generator GDP and doing so in sync with the control of the pressurized jet.

In certain cases and depending on the value of the repetition rate $F_R$, it may be possible to make do with communication with the atmosphere, i.e., a periodic aeration in sync with the pressure pulses of the pressurized liquid feed tube 2. This aeration may be total, partial, or reduced by means of a controlled or automatic aeration device. In these cases, this technique will thus enable simple reestablishment of the shape of the decaying edge of the pressure pulse, i.e., reestablishment of a clean, steep slope.

Figure 6:
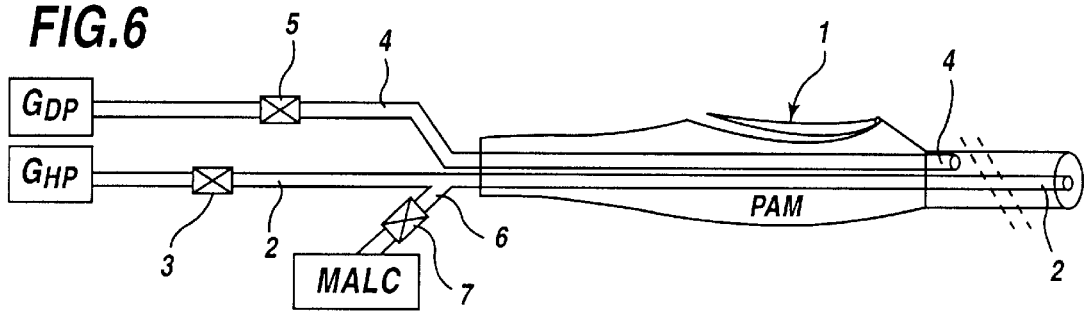
FIGS. 6 and 7 are similar views but with a link to a controlled aeration device MALC or an automatic aeration device MALA.

As depicted in FIG. 6, this may be a controlled escape aeration element MALC which may or may not include the switching device 7.

By way of example, a controlled valve or a permeable membrane or any other similar means may be cited.

Figure 7:
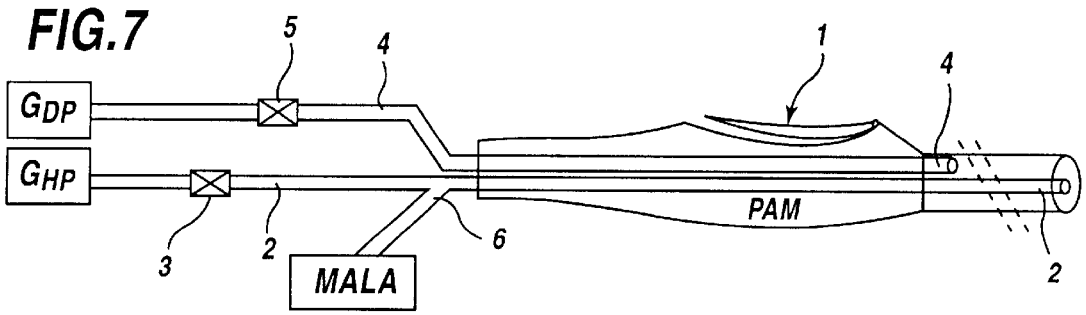
Figure 8:
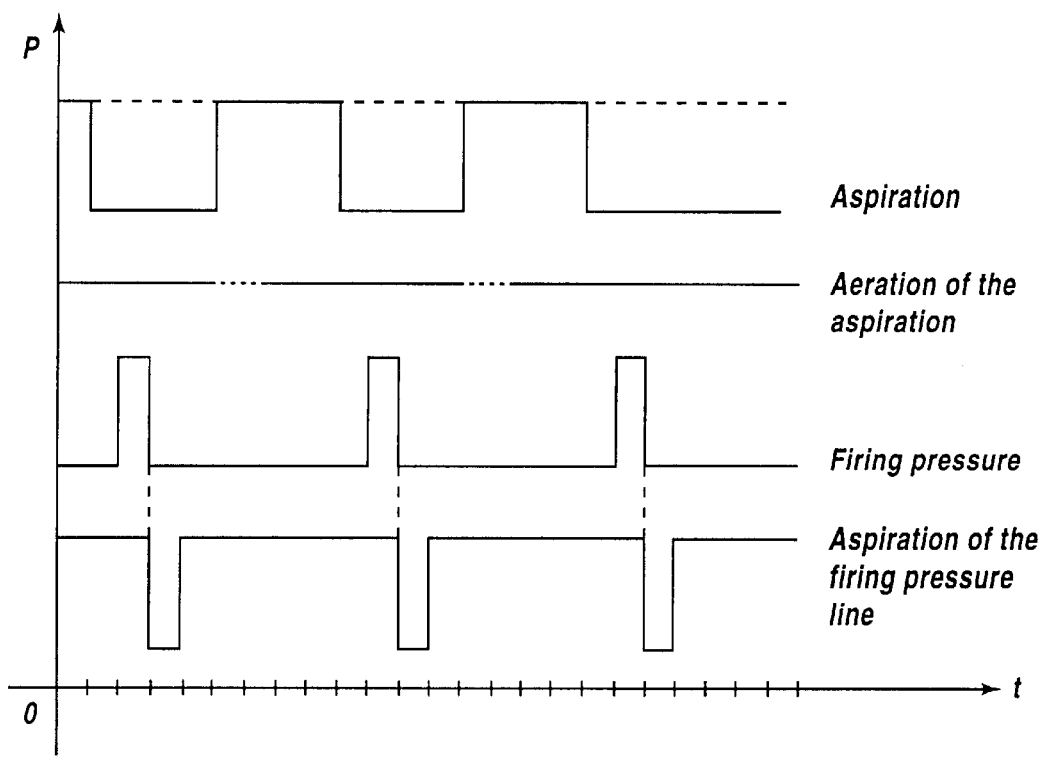
FIG. 8 is a graphic of the waveforms of various magnitudes of pressure P forming the pulsed jet represented as a function of the time "t" with periodic aeration.
Figure 9:
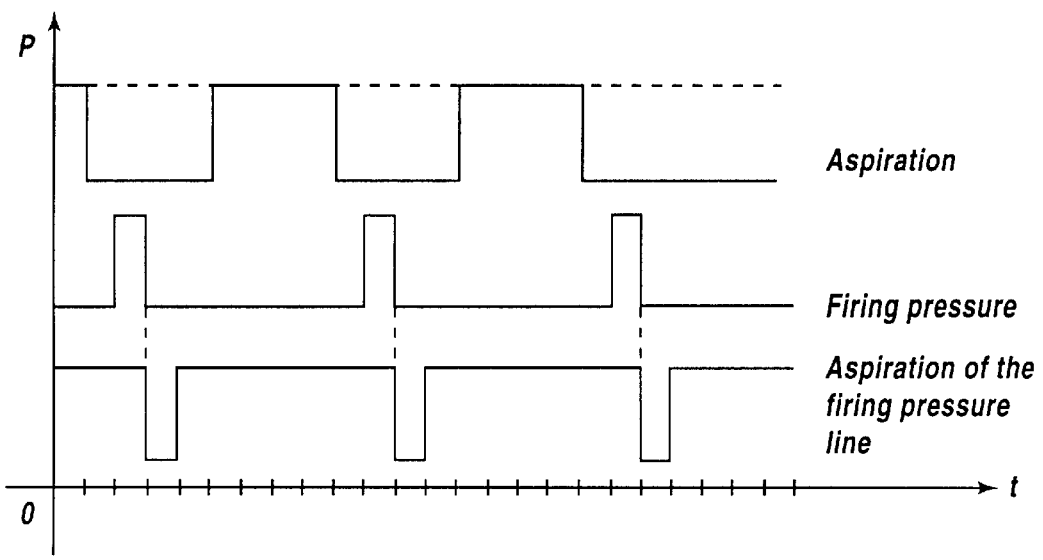
FIG. 9 is a graphic of the waveforms of various magnitudes of pressure P forming the pulsed jet represented as a function of the time "t" without periodic aeration.

As depicted in FIG. 7, this may also be an automatic aeration element, i.e., an automatic escape. By way of example, a calibrated valve with a delay effect may be cited.

Thus, the residual pressure may be evacuated simply and automatically through an adjacent outlet connected to an MALA device with a pressure threshold or with a constant periodic opening delay.

Of course, the term "exterior" must be interpreted in its most general sense, i.e., a space or volume outside the feed line 2. In effect, it may also be a buffer volume, a closed expandable volume, a flexible membrane, or the like.

It is also possible to control this cutoff by establishing communication of the pressure line 2 with the depression generator GDP. It suffices to control the opening of the communication with the exterior through the branched offshoot 6 of the pressurized liquid feed line 2 shortly before cutoff of the pressurized liquid.

Figure 10:
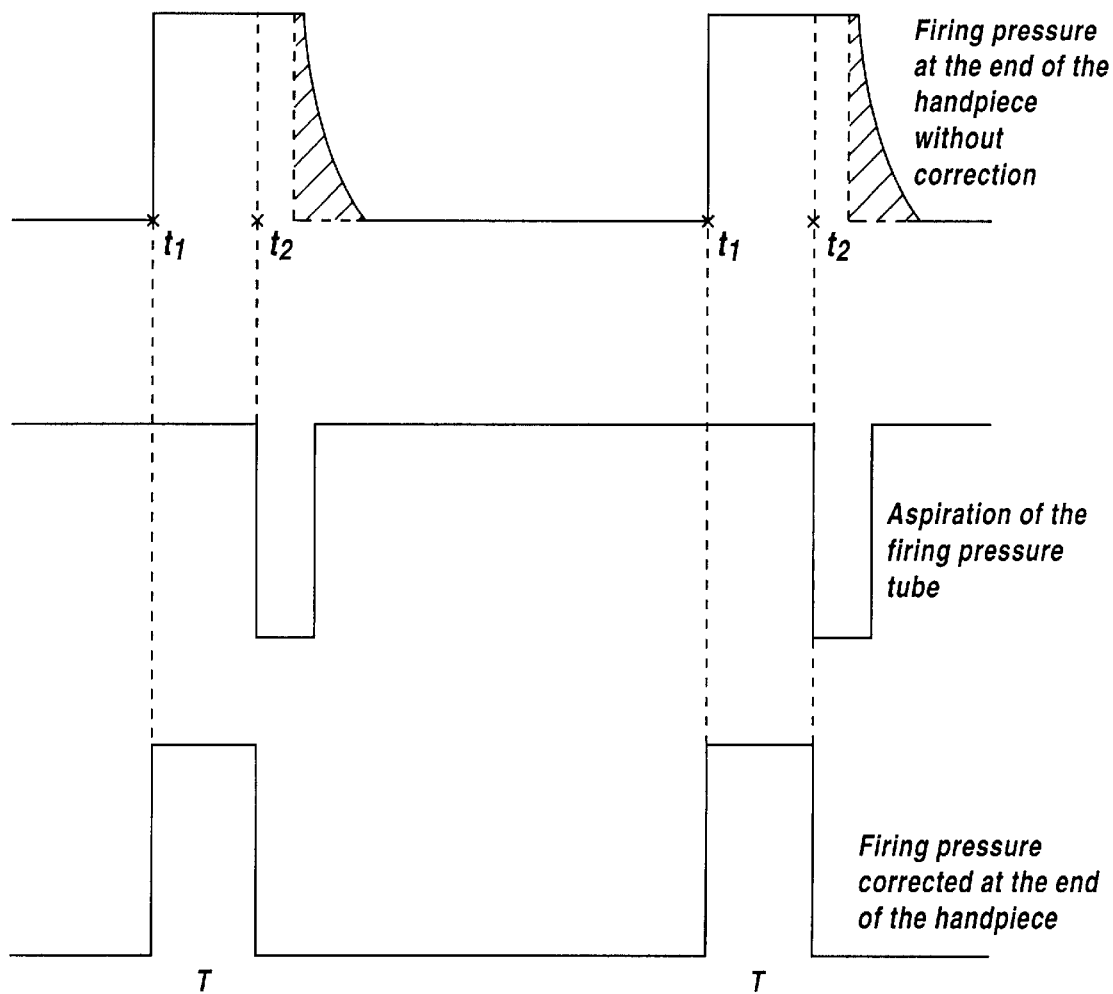
FIG. 10 is a graphic of the waveforms of the different magnitudes of pressure P forming the pulsed jet represented as a function of the time "t" with control of the trailing edge of the drop in pressure after aspiration.

This mode of operation which will now be described is depicted in FIG. 10.

According to the major characteristic of the basic process, firing is effected during the aspiration phase, i.e., the pressure pulse is triggered and cut off within the interval of time corresponding to a depression period.

FIG. 10 depicts the control of aeration of the aspiration which occurs immediately after the cutoff of the aspiration to favor tissue relaxation and dislodging.

The second part of FIG. 10 depicts control of the end of firing by aspiration.

The firing pressure pulse without correction at the end of the handpiece is depicted by the third curve with the inefficiency zone indicated by hatching.

According to this variant, the firing pulse cutoff is controlled by the depression before its normal cutoff by the opening-closing element 3.

More specifically, according to the present variant, the pressure pulse beginning at the time t1 is cut off in advance at the time t2 by means of rapid controlled opening of the communication with the exterior, in particular with the aspiration. The firing pulse is thus calibrated to a duration T by implementing a steep, clean cutoff as depicted in the last waveform shown in this FIG. 10.

The duration of the depression or aspiration pulse of the firing pressure line which triggers the cutoff (curve 4) is adequate to realize the complete discharge of the residual pressure. It nevertheless remains short.

The purpose of the depression or aspiration pulse is to create suction for the liquid and thus a discharge before or immediately before the cutoff of the liquid pressure, thus neutralizing the pressure remnant and ensuring a abrupt drop in pressure.

The present invention is actuated by a pressurized liquid source and by a device for sequencing, i.e., abrupt stopping and starting of the pressurized liquid jet feeding a handpiece or a catheter.

The formation of the pulses may result from repetitive mechanical actions, for example, on a flexible line.

In the standard mode of operation, i.e., regular, the pulse train triggered by the operator continues at the repetition rate $F_R$ until the manual stop control issued by the operator.

In different application cases, it is advantageous to limit the number of elementary pressurized liquid jets by other means and automatically. A specialized control and count-up/count-down program is used. By digital control on the handpiece, the operator will trigger a limited number of elementary pressurized liquid jets in succession at the repetition rate $F_R$. This sequence will stop automatically when the programmed number of firing pulses has been reached.

The number of elementary pressurized liquid jets is limited only by practical considerations associated with the intervention and by the hardware and software capabilities.

It is also conceivable to program only a single firing of an elementary pressurized liquid jet. In this case, the operator will trigger only a single firing with his manual control. The next firing will have to be triggered by a new command.

What is claimed is:

1. Process for controlled generation of a pulse train of a pulsed liquid jet for a handpiece, particularly for surgical and medical applications, by successive periodic commands at a repetition rate $F_R$ of firing of elementary pressurized liquid jets implementing a pressurized liquid channel from a pressurized liquid generator GHP and an aspiration channel connected to a source of depression GDP characterized in that the firing of elementary jets is controlled by periodically cutting the flow of the pressurized liquid feeding the handpiece according to the repetition rate $F_R$ and before the end of each repetition period, thus forming periodic firing pulses, the aspiration is controlled periodically at the same repetition rate $F_R$, and the aspiration is periodically cut at the same repetition rate $F_R$ before the next periodic command of the next periodic firing pulse of the pressurized liquid, forming periodic aspiration pulses longer in duration than the periodic firing pulses, a firing pulse is controlled within each aspiration pulse, thus creating a pulsed-aspirated jet.

2. Process according to claim 1, characterized in that the pressurized liquid is generated and expelled under high pressure.

3. Process according to claim 1, characterized in that the high pressure is between 10 and 100 bar.

4. Process according to claim 1, characterized in that the periodic firing of the pressurized jet is controlled in the first half of the periodic duration of application of aspiration.

5. Process according to claim 1, characterized in that the periodic firing duration of the pressurized jet ends before the first half of the periodic aspiration pulse.

6. Process according to claim 1, characterized in that the aspiration is followed after being cut off by a compensation of the suction effect to relax the tissue.

7. Process according to claim 1, characterized in that the compensation of the suction effect is aeration during the cutoff in aspiration.

8. Process according to claim 1, characterized in that aeration is carried out through the aspiration line.

9. Process according to claim 1, characterized in that the repetition rate $F_R$ can be modified.

10. Process according to claim 1, characterized in that the repetition rate $F_R$ is within a range between a fraction of a hertz and a few hertz.

11. Process according claim 1, characterized in that the repetition rate $F_R$ is between 0.1 and 10 Hz.

12. Process according to claim 1, characterized in that the repetition rate $F_R$ is on the order of 1 Hz.

13. Process according to claim 1, characterized in that the trailing edge of the pressure pulse P is obtained, near the time of the cutoff of the feed of pressurized liquid, by discharging the pressurized liquid feed line of the handpiece PAM by the establishment of communication of this line with an exterior.

14. Process according to claim 1, characterized in that the establishment of communication with the exterior is the establishment of communication with a depression generator GDP.

15. Process according to claim 1, characterized in that establishment of communication with the exterior is aeration.

16. Process according to claim 1, characterized in that the establishment of communication with the exterior which is effected near the time of the cutoff is a discharge into a buffer volume.

17. Process according to claim 1, characterized in that the establishment of communication with the exterior which is effected near the time of the cutoff is a discharge into an expandable closed volume.

18. Process according to claim 1, characterized in that the establishment of communication with the exterior is effected slightly before the cutoff.

19. Process according to claim 1, characterized in that the establishment of communication with the exterior is effected at the time of the cutoff.

20. Process according to claim 1, characterized in that the establishment of communication with the exterior is effected shortly after the cutoff.

21. Process according to claim 1, characterized in that the period of the aspiration discharging the feed tube (2) is short relative to the period between the trailing edge of the pressure pulse and the leading edge of the next pressure pulse.

22. Process according to claim 1, characterized in that the cutoff of the liquid pressure pulse is controlled by controlling the establishment of communication with the depression generator GDP.

23. Process according to claim 1, characterized in that a specific number of elementary pressurized liquid jets is controlled.

24. Process according to claim 1, characterized in that a single elementary pressurized liquid jet is controlled at one time.

25. Pulsed-aspirated liquid jet for a handpiece, in particular for surgical applications, which is obtained by the process according to claim 1.

* * * * *